United States Patent [19]
Melzer et al.

[11] Patent Number: 5,099,827
[45] Date of Patent: Mar. 31, 1992

[54] INSTRUMENT SET FOR CLOSING OPENED BODY ORGANS, WOUNDS OR THE LIKE

[75] Inventors: Andreas Melzer, Wiesbaden; Gerhard F. Buess, Tübingen; Carsten N. Gutt, Mainz, all of Fed. Rep. of Germany

[73] Assignee: Richard Wolf GmbH, Knittlingen, Fed. Rep. of Germany

[21] Appl. No.: 621,505

[22] Filed: Dec. 3, 1990

[30] Foreign Application Priority Data

Dec. 13, 1989 [DE] Fed. Rep. of Germany ....... 3941108

[51] Int. Cl.⁵ .............................................. A61B 1/00
[52] U.S. Cl. .......................................... 128/4; 128/6; 606/142
[58] Field of Search ......................................... 128/4–6, 128/7; 606/142

[56] References Cited

U.S. PATENT DOCUMENTS

| | | | |
|---|---|---|---|
| 4,421,106 | 12/1983 | Uehara | 128/4 |
| 4,538,594 | 9/1985 | Boebel et al. | 128/6 |
| 4,653,476 | 3/1987 | Bonnet | 128/4 |
| 4,685,449 | 8/1987 | Bonnet | 128/4 |
| 4,686,965 | 8/1987 | Bonnet et al. | 606/4 |

FOREIGN PATENT DOCUMENTS 3713830 12/1988 Fed. Rep. of Germany .

Primary Examiner—Stephen C. Pellegrino
Assistant Examiner—Gary Jackson
Attorney, Agent, or Firm—Panitch Schwarze Jacobs & Nadel

[57] ABSTRACT

An instrument set comprises an outer tube and an inner tube projecting distally over the outer tube, between which at least two channels for retaining forceps extend, an observation optical system which can be introduced through the inner shaft, dilators to widen the opening in the organs, wounds or the like, a working optical system having a channel for instruments to be introduced and which can be exchanged for the observation optical system, and a clip applicator having a clip which can be pushed onto the clip applicator and can be pushed off in the distal direction for closing a dilated opening in organs, wounds and the like.

12 Claims, 5 Drawing Sheets

INSTRUMENT SET FOR CLOSING OPENED BODY ORGANS, WOUNDS OR THE LIKE

BACKGROUND OF THE INVENTION a) Field of the Invention

The invention relates to an instrument set in accordance with German Patent No 3504292 which corresponds to U.S. Pat. No. 4,686,965.

b) Description of the Prior Art

An instrument set for percutaneous removal of gall stones is described in German Patent No 3504292, which comprises an outer tube, that can advantageously be fixed, having channels for forceps to be introduced to grip the gall bladder, and an inner tube for a working optical system to be passed through and for introducing instruments for the removal of gall stones.

Only one, unsatisfactory, cleaning step, disinfection and sterilisation is possible as a result of the arrangement of the forceps channels on the trocar sleeve as an outer tube. Moreover, there is no possibility of retaining the tissue portion of the gall bladder securely without difficulty and being able to handle the requirements appropriately and to close the relatively large incision to be made in the gall bladder again in a sealed manner without difficulty after removing the gall stones.

Accordingly, the main object of the present invention is to provide an instrument set by means of which the aforesaid disadvantages are minimized or prevented and above all to achieve secure closing of opened hollow organs, wounds or the like, such as for example the incision of the gall bladder, without having to undertake a further puncture in the body cavity for the introduction of an appropriate closing instrument.

SUMMARY OF THE INVENTION

To this end, the present invention consists in an instrument set for closing opened hollow organs, wounds or the like, comprising an outer tube and an inner tube fixed non-releasably to said outer tube, channels for forceps to be passed through to grip a hollow organ, edges of a wound or the like, and a working optical system to be passed through the inner tube which has an channel to introduce auxiliary instruments and the like, characterised in that at least two channels for retaining forceps extend between the outer tube and the inner tube with said inner tube projecting distally beyond the outer tube, in that an observation optical system which can be introduced through the inner tube and an aspirating probe having a removable puncture needle are provided, in that dilators for widening an incision in a hollow organ can be exchanged for the probe, and in that an observation optical system is provided and can be exchanged for the working optical system which can be fixed releasably in the inner tube, and having a channel for auxiliary instruments to be introduced, and a clip applicator having a clip which can be pushed onto the clip applicator distally and can be removed in a distal direction, for closing an opened hollow organ, a wound or the like. As a result of the solution according to the invention it is possible to guide the tissue of the hollow organ or the like to the hollow organ, after introducing the instrument comprising the outer tube and inner tube having retaining forceps while observing the body cavity through the abdominal wall by means of a working optical system, and to securely grip and retain the tissue of the hollow organ at two, advantageously at four, diagonally opposed points by means of the forceps. The incision may then be made by means of an aspirating probe having a puncture needle and the incision widened by means of dilators and then the incision may be closed by means of the clip applicator. The design according to the invention enables satisfactory cleaning, disinfection and sterilisation of all parts to be carried out, and makes it possible to manipulate the securely gripped tissue of the gall bladder and then to remove the gall stones and to close the incision in the gall bladder made by the incision needle again by means of an applicator and a clip.

Preferably the channels extending between the outer and inner tubes are bent outwards proximally, and have a seal for proximally actuated, semi-rigidly designed retaining forceps, the two distal mouth part jaws of which have a hook shape and are each guided in a groove.

In one embodiment of the invention, a plane which extends transversely to the plane of the mouth of the retaining forceps may form an angle with the longitudinal axis of the forceps.

In another embodiment of the invention, the channel formed through the inner tube is sealed proximally by a seal and is provided with a closable tap to feed and remove rinsing liquid or gas from the body cavity.

The outer tube may be provided with a handle, having a rigid extension which can be fixed.

Preferably, a first dilator for widening an incision made by means of a puncture needle comprises a cone divided in the axial direction into hinge-connected halves which can be opened by means of a proximal handle.

The two halves of the cone may be provided on both sides with opposing depressions into which the edges of the wound of the opened organ or the like engage.

In addition to the first dilator, a second dilator having a rigid cone and having a central channel may be provided for introducing the observation optical system which can be coupled to the proximal end of the dilator.

Advantageously, the aspirating probe comprises a puncture needle which can be coupled proximally with a rinsing and suction pipe and can be connected proximally with a hose connection which can be changed over, and the suction pipe has a pipe widening device at its distal end.

In a preferred embodiment of the invention, the clip applicator has a mouth which can be closed by means of a proximal handle, the mouth limbs of this mouth being provided with gripping teeth facing one another and in each case stop pairs on both sides for arresting the two projections of the clip and, on the proximal side of the forceps mouth, a plastically deformamble clip guided in two opposing grooves having decreasing depth in the proximal direction can be pushed on and can be releasably fixed, which clip can be deformed by means of an outer shaft which can be pushed onto the applicator for closing the opened hollow organ, a wound or the like, and subsequently after opening the two mouth limbs can be released by means of the applicator.

Conveniently, the clip which can be gripped by the applicator has a recess which is provided with two opposing projections coming to rest against the stop pairs of the mouth limbs by pushing the clip by means of the outer shaft.

The outer shaft which can be moved longitudinally on the applicator may be provided distally on both sides with a V-shaped cut-out.

BRIEF DESCRIPTION OF THE DRAWINGS

In order that the invention may be more readily understood, an embodiment of instrument set will now be described, by way of example, to the accompanying drawings, in which.

DESCRIPTION OF THE PREFERRED EMBODIMENT

Figure 1:
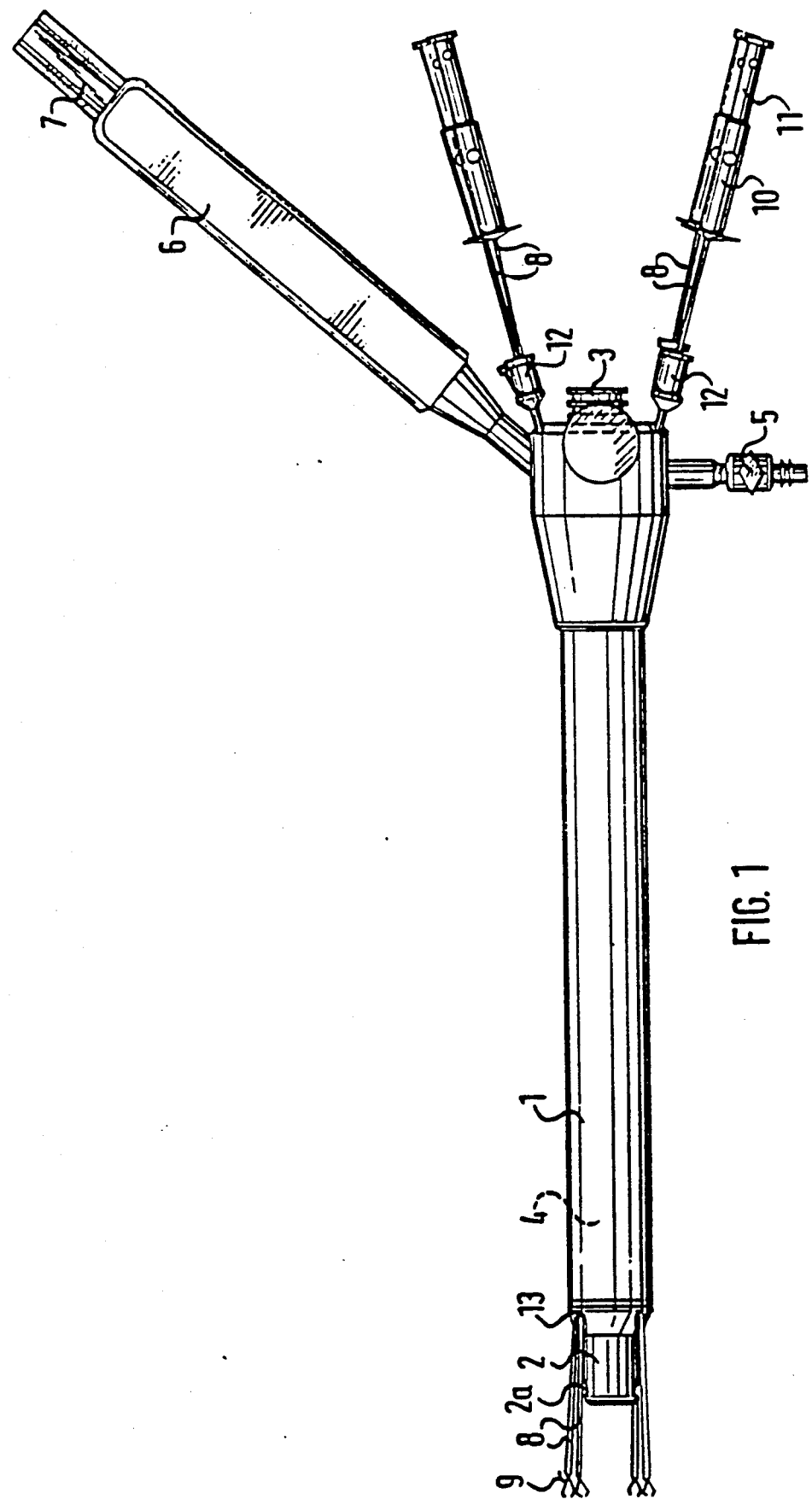
FIG. 1 shows a side view of an outer tube having an inner tube and retaining forceps.

The instrument set shown comprises according to FIG. 1 an outer tube 1 having an inner tube 2 fixed non-releasably therein, and having distal openings 2a to monitor the correct position of the tissue to be pulled over the inner tube 2. The inner tube 2 projects distally in relation to the outer tube, and has a channel 4 sealed proximally by means of a seal 3. There exists the possibility of introducing gas or a rinsing liquid into the body cavity via the channel 4 and of removing the latter by suction along with any secretions or the like as a result of the sealable connection pieces 5. The outer tube 1 is provided proximally with a handle 6 having a rigid extension 7 which may be attached to a fixed device, for example by means of a lockable hinged arm or the like, to an operating table in order to be able to retain the tube or the entire instrument fixed in place for the operation.

Two, advantageously four, diagonally opposed channels in a rectangle extend between the outer and inner tubes, through which channels semi-rigidly designed forceps 8 extend to retain the gall bladder. The forceps 8 each have mouth limbs 9, which are preferably both hook-shaped and guided in a groove and can be actuated by proximal, spring-tensioned handle parts 10 and 11. The forceps 8 pass through proximal seals 12 in channels 13 and extend outwardly at their distal and proximal ends at an angle to the longitudinal axis of the tube 1 on the one hand to be able to manipulate the tissue with regard to its position relative to the mouth part of the applicator, and on the other hand to make handling easier.

Figure 7:
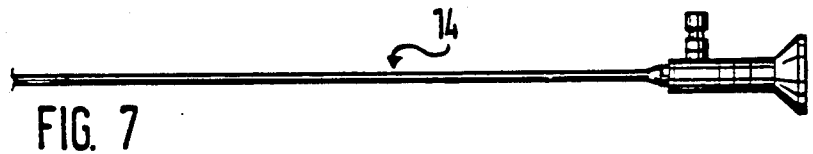
FIG. 7 shows a side view of a conventional observation optical system.
Figure 8:
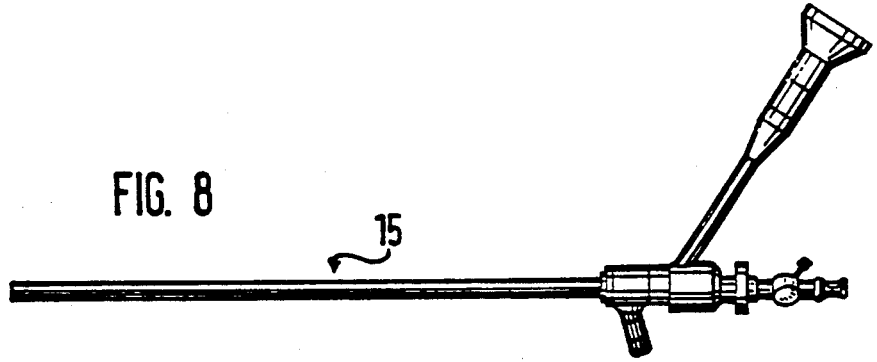
FIG. 8 shows a side view of a known working optical system.
Figure 9:
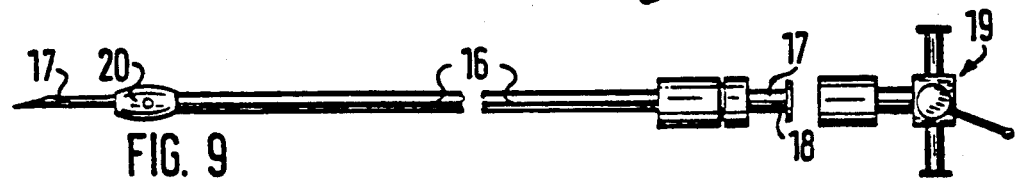
FIG. 9 shows a side view of an aspirating probe having a puncture needle and a rinsing and suction connection which can be coupled and switched over.
Figure 10:
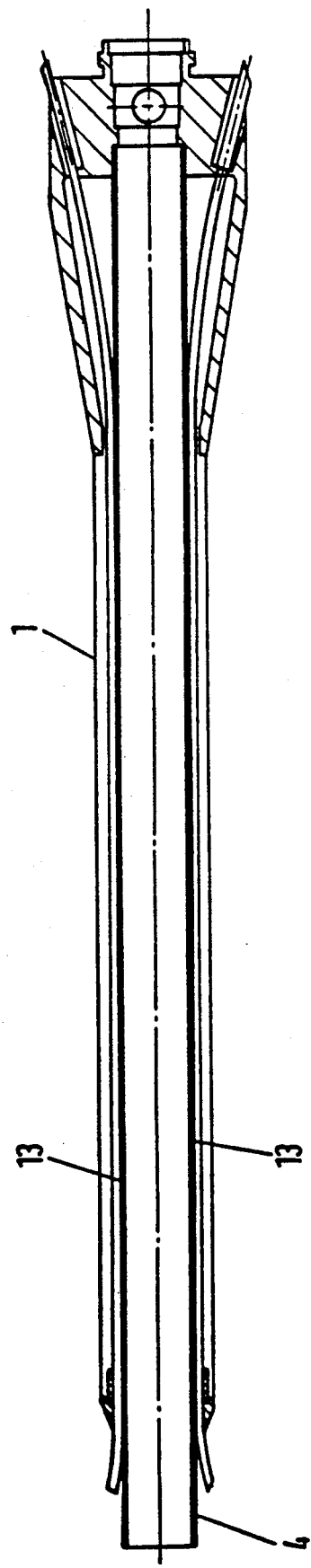
FIG. 10 shows a cross-sectional view of the device of FIG. 1 taken along the longitudinal axis thereof.
Figure 11:
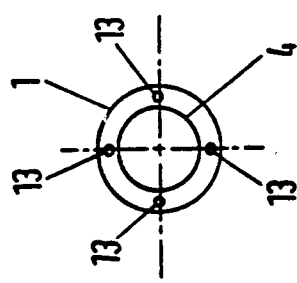
FIG. 11 is a left elevational view of the device shown in FIG. 10.
Figure 12:
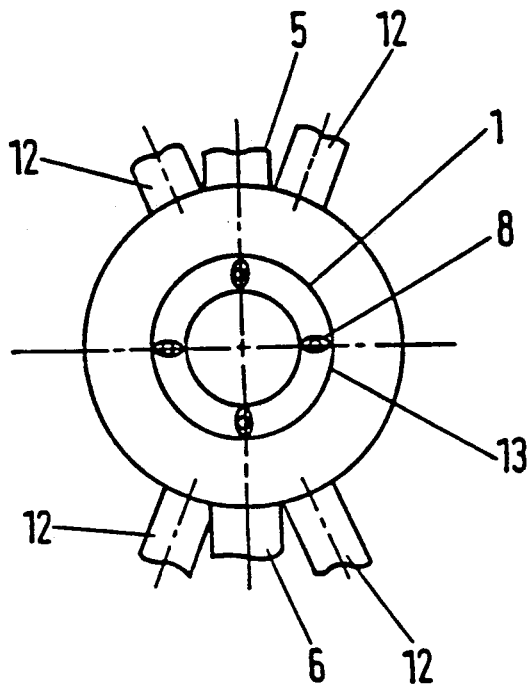
FIG. 12 is a left elevational view of the device of FIG. 1 showing the distal end thereof.
Figure 13:
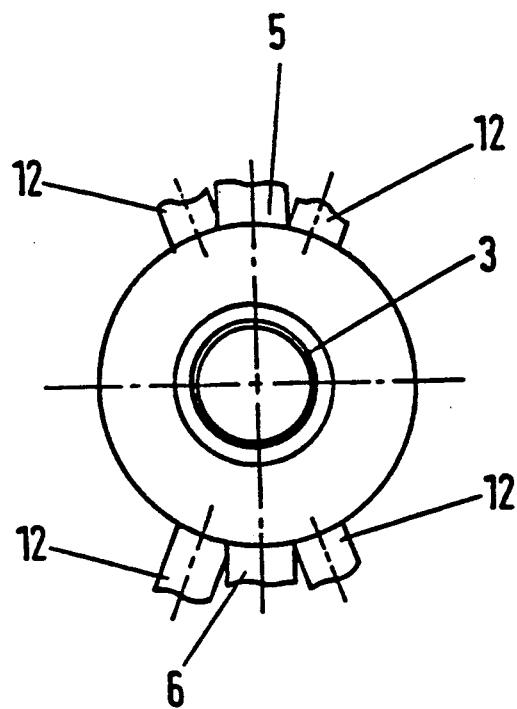
FIG. 13 is a right elevational view of the device shown in FIG. 1 showing the proximal end thereof.

The instrument set also comprises a known observation optical system 14 (See FIG. 7) and a working optical system 15 (See FIG. 8) with a channel running therethrough for instruments to be introduced and also an aspirating probe according to FIG. 9 through the shaft of which a puncture needle 17, which can be coupled, and having a proximal hose connection 18 is guided, and which can be connected proximally via a connection 19, which can be switched over, to a feed and outlet for a rinsing liquid.

The pipe of the probe 16 is provided distally with a pipe widening device 20.

Figure 2A:
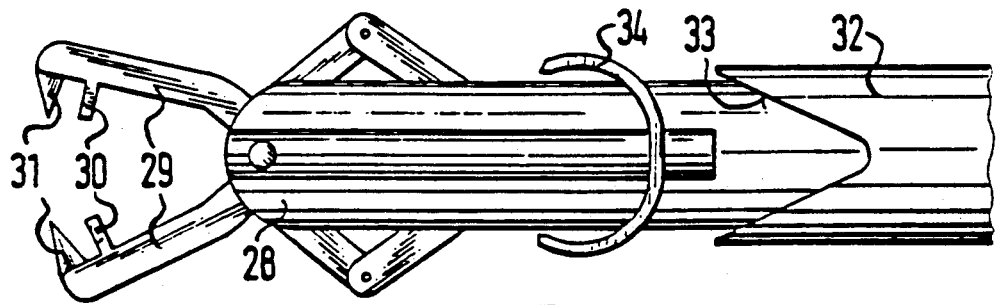
FIG. 2a and 2b show the enlarged end of a clip applicator with opened and closed mouth in side view.
Figure 2B:
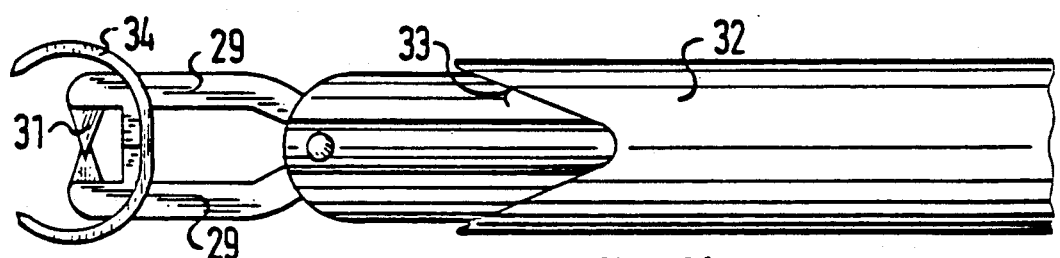
Figure 2C:
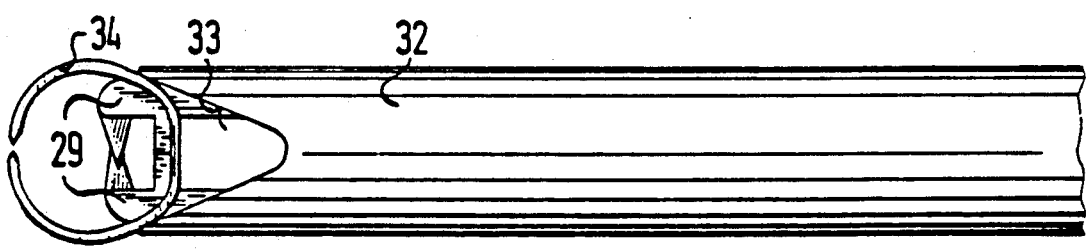
FIG. 2c shows the same clip applicator having an outer shaft pushed forward in the distal direction.
Figure 3:
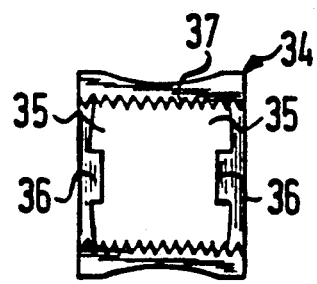
FIG. 3 shows a clip seen in the direction opposite to its open end.
Figure 4:
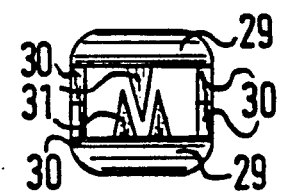
FIG. 4 shows an end view opposite to the distal closed end of the applicator mouth.
Figure 5A:
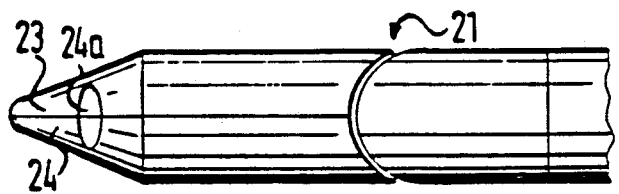
FIGS. 5a and 5b show a first dilator in two enlarged side views turned by 90°.
Figure 5B:
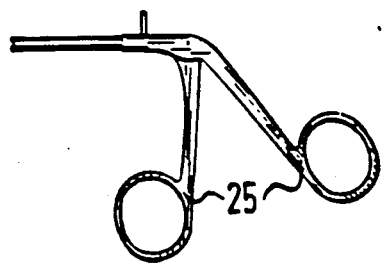
Figure 5B:
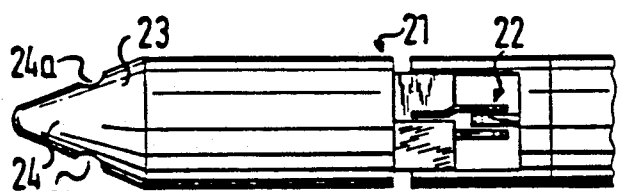
Figure 6:
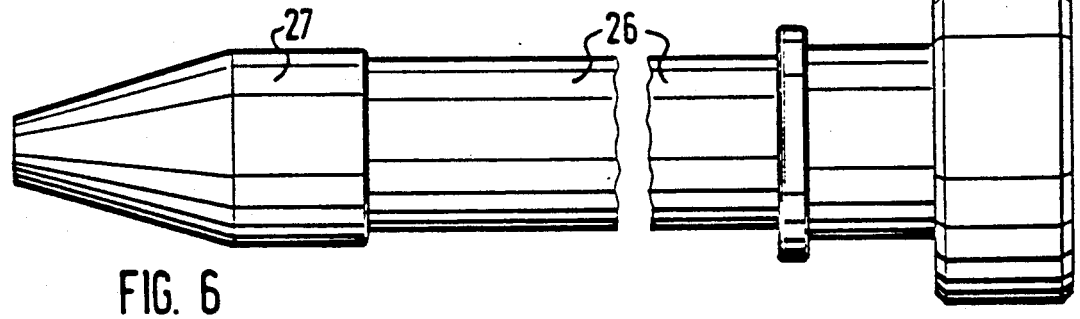
FIG. 6 shows a side view of a second dilator.

The instrument set also comprises two dilators according to FIGS. 5a, 5b and 6 and a clip applicator according to FIGS. 2, 3 and 4.

The first dilator 21 according to FIGS. 5a and 5b comprises two cone halves 23 and 24 connected by means of a hinge 22, which cone halves 23 and 24 may be opened by means of a scissor handle 25. The second dilator 26 comprises a rigid cone 27 having a shaft and is provided with a through channel for an observation optical system 14 according to FIG. 7 which may be coupled together with the dilator.

The clip applicator according to FIGS. 2 to 4 comprises a shaft 28, in the distal end of which the two mouth limbs 29 are pivoted by means of a proximal handle not shown. The mouth limbs 29 are held in the closed position parallel and at a distance by means of lateral stop pairs 30 and are provided with teeth 31 facing one another. An outer shaft 32 having a distal V-shaped cutout 33 is positioned so it can be pushed longitudially on the shaft 28, a deformable clip 34 which is pushed onto the shaft 28 until it is behind the mouth hinge is plastically deformed as a result of this V-shaped cutout 33 in an application position according to FIG. 2b and then is plastically deformed to close the dilated gall bladder incision, as is explained in further detail.

The clip 34 is provided with a perforation 35 through which the applicator can be pushed to grip the two stops with a slightly opened mouth until it has reached a position according to FIG. 2a. The clip is also provided with inwardly directed projections 36 which come to rest against the stop 30 of the mouth limbs 29 when the clip is pushed in the distal direction through the outer shaft 32 and into the application position according to FIG. 2b. The two clip limbs 37 have teeth on the inner sides facing one another.

The method of operation of the instrument set according to the invention described above is as follows.

The instrument according to FIG. 1 together with the working optical system according to FIG. 8 and the aspirating probe according to FIG. 9 is introduced into the body cavity through the abdominal wall of a patient, and then the gall bladder is gripped and retained at four points lying in a rectangle by means of the four forceps 8 while being observed. An incision is then made in the gall bladder by means of the puncture needle 17 and a certain amount of gall fluid is removed under suction. After removing the puncture needle, the bile is rinsed after introducing the distal end 20 of the probe into the gall bladder.

The pipe of the probe 16 is then removed from the gall bladder and from the channel for the working optical system 15, and the probe is replaced by the first dilator 21 according to FIGS. 5a and 5b, by means of which the incision in the gall bladder made by the puncture needle 17 is widened using the dilator cone 23, 24 to be opened. The dilator 21 and the working optical system 15 are then replaced by the second dilator 26 with the observation optical system 14 passed through it according to FIG. 7 and the incision in the gall bladder is widened further, the gall bladder being gripped by the forceps 8 being pulled onto the rigid cone 27. The forceps 8 are thus rotated about their longitudinal axis so that the folds of the bladder which are gripped occupy a plane parallel or approximately parallel to the circumference of the dilator.

The second dilator 26 with the observation optical system 14 is then removed and replaced by the working optical system 15 through which the fragmention and/or removal of a gall stone then takes place.

The clip applicator according to FIG. 2a is then passed through the working optical system with closed mouth removed from the tube 1, 2, whereupon the clip 34 is pushed in the distal direction through the outer shaft 32 into the application position according to FIG. 2b. The outer shaft 32 is then pushed further in the distal direction so that the limbs of the release clip 34 then grip and compress the bladder tissue using the clip teeth in a deforming manner as a result of the V-shaped cut-out 33, whereupon the incision is then closed satisfactorily. The clip applicator is then opened after pulling back the movable outer shaft 32 and is pulled out with the working optical system, and the tube 1, 2 is then also removed from the body cavity.

Whilst a particular embodiment has been described it should be appreciated that the invention is not limited thereto but includes all modifications and variations falling within its scope.

What is claimed is:

1. An instrument set for closing opened hollow organs and wounds having edges, comprising an outer tube and an inner tube fixed non-releasably to and within the outer tube, two channels between the outer tube and the inner tube for forceps to be passed through to grip the edges, said inner tube having a channel to introduce auxiliary instruments, said inner tube projecting distally beyond the outer tube, said channel of said inner tube receiving therethrough at least one of an observation optical system, an aspirating probe having a removable puncture needle, a dilator for widening an incision in a hollow organ, a working optical system having a channel for auxiliary instruments to be introduced therethrough, and a clip applicator for receiving a clip which can be pushed onto the clip applicator distally and can be removed in a distal direction, for closing opened hollow organs and wounds.

2. An instrument set according to claim 1, wherein channels extending between outer and inner tubes are bent outwards proximally and have a seal for proximally acutated, semi-rigidly designed retaining forceps having two distal mouth part jaws which are of hook shape and which are each guided in a groove.

3. An instrument set according to claim 2, wherein the retaining forceps have a longitudinal axis and wherein a place which extends transversely to a plane of the mouth of the retaining forceps forms an angle with the longitudinal axis of the forceps.

4. An instrument set according to claim 1, wherein the channel through the inner tube is sealed proximally by a seal and is provided with a closable tap for feeding and removing rinsing fluid from a body cavity.

5. An instrument set according to claim 1, wherein the outer tube is provided with a handle having a rigid extension.

6. An instrument set according to claim 1, wherein the dilator includes a puncture needle comprising a cone which is axially split into hinged-connected halves which are separable by a proximal handle.

7. An instrument set according to claim 6, wherein the two halves of the cone are provided on both sides with opposing depressions in which the edges engage.

8. An instrument set according to claim 6, further including a second dilator having a proximal end, a rigid cone and having a central channel for receiving an observation optical system therethrough to be coupled to the proximal end of the second dilator.

9. An instrument set according to claim 1, wherein the aspirating probe comprises a puncture needle coupled proximally with a rinsing and suction pipe and connected proximally with a hose connection, wherein the sunction pipe has a distal end and a pipe widening device at the said distal end thereof.

10. An instrument set according to claim 1, wherein the clip applicator has a mouth closeable by a proximal handle and mouth limbs provided with gripping teeth facing one another, each mouth limb having stop pairs on both sides thereof for arresting two projections of a clip and wherein on the proximal side of the forceps a plastically deformable clip is guided in two opposing grooves having decreasing depth in a proximal direction, said clip being deformed by means of an outer shaft which is pushed onto the applicator for closing opened hollow organs and wounds, and subsequently after opening the two mouth limbs are releasable by the applicator.

11. An instrument set according to claim 10, wherein the clip has a recess provided with two opposing projections which abut against the stop pairs of the mouth limbs by pushing the clip with the outer shaft.

12. An instrument set according to claim 10, wherein the outer shaft is movable longitudinally on the applicator and is provided distally on both sides with a V-shaped cut-out.

* * * * *